United States Patent
Mercuri et al.

(10) Patent No.: US 11,009,599 B2
(45) Date of Patent: May 18, 2021

(54) METHOD AND A SYSTEM FOR LOCALIZATION AND MONITORING OF LIVING BEING TARGETS

(71) Applicant: STICHTING IMEC NEDERLAND, Eindhoven (NL)

(72) Inventors: Marco Mercuri, Leuven (BE); Ilde Rosa Lorato, Leuven (BE)

(73) Assignee: STICHTING IMEC NEDERLAND, Eindhoven (NL)

(*) Notice: Subject to any disclaimer, the term of this patent is extended or adjusted under 35 U.S.C. 154(b) by 234 days.

(21) Appl. No.: 16/026,465

(22) Filed: Jul. 3, 2018

(65) Prior Publication Data
US 2019/0011549 A1   Jan. 10, 2019

(30) Foreign Application Priority Data
Jul. 5, 2017   (EP) .................................... 17179826

(51) Int. Cl.
*G01S 13/72* (2006.01)
*G01S 13/536* (2006.01)
(Continued)

(52) U.S. Cl.
CPC .............. *G01S 13/72* (2013.01); *A61B 5/024* (2013.01); *A61B 5/0507* (2013.01);
(Continued)

(58) Field of Classification Search
CPC ...... G16H 40/63; A61B 5/024; A61B 5/0507; A61B 5/0816; G01S 7/352; G01S 7/415;
(Continued)

(56) References Cited

U.S. PATENT DOCUMENTS 6,150,976 A * 11/2000 Cooley ................. G01S 7/4052
342/165
7,064,702 B1 * 6/2006 Abatzoglou ........ G01S 13/9019
342/25 F
(Continued)

FOREIGN PATENT DOCUMENTS

WO   WO-2015184406-A1   12/2015

OTHER PUBLICATIONS

Wang et al., "Application of Linear-Frequency-Modulated Continuous-Wave (LFMCW) Radars for Tracking of Vital Signs", IEEE Transactions on Microwave Theory and Techniques, vol. 62, Issue 6, pp. 1387-1399, Jun. 2014.
(Continued)

*Primary Examiner* — Vladimir Magloire
*Assistant Examiner* — Alexander L. Syrkin
(74) *Attorney, Agent, or Firm* — Moser Taboada

(57) ABSTRACT

A method for localization and monitoring of living being targets in an environment comprise: transmitting (302) a sequence of radio frequency waveforms, the waveforms being a continuous-wave waveform modulated in frequency and/or phase; detecting (304) a sequence of reflected waveforms being reflected by a target and Doppler-shifted due to a movement of the target, forming (306) a sequence of waveform transforms, wherein the waveform transform comprises discretized information in a plurality of range bins, and wherein the information in a single range bin corresponds to reflections occurring at a specific sector in the environment; analyzing (308) information for a single specific sector in a sub-sequence of the sequence of waveform transforms, and determining (310) movement of a target in the specific sector based on the waveform transform information for that specific sector during a time period corresponding to the sub-sequence.

16 Claims, 12 Drawing Sheets

(51) Int. Cl.
| | |
|---|---|
| *G01S 13/58* | (2006.01) |
| *G16H 40/63* | (2018.01) |
| *A61B 5/024* | (2006.01) |
| *G01S 7/35* | (2006.01) |
| *G01S 13/88* | (2006.01) |
| *G01S 7/41* | (2006.01) |
| *A61B 5/08* | (2006.01) |
| *G01S 13/66* | (2006.01) |
| *A61B 5/0507* | (2021.01) |
| *A61B 5/05* | (2021.01) |

(52) U.S. Cl.
CPC ............ *A61B 5/0816* (2013.01); *G01S 7/352* (2013.01); *G01S 7/415* (2013.01); *G01S 13/536* (2013.01); *G01S 13/583* (2013.01); *G01S 13/584* (2013.01); *G01S 13/66* (2013.01); *G01S 13/88* (2013.01); *G16H 40/63* (2018.01); *G01S 2007/356* (2013.01)

(58) Field of Classification Search
CPC .... G01S 13/536; G01S 13/583; G01S 13/584; G01S 13/66; G01S 13/88; G01S 2007/356; G01S 13/72
USPC ........................................................ 342/109
See application file for complete search history.

(56) References Cited

U.S. PATENT DOCUMENTS

| | | | |
|---|---|---|---|
| 7,567,200 B1* | 7/2009 | Osterweil | A61B 5/1117 342/28 |
| 9,746,549 B1* | 8/2017 | Parker | G01S 7/2922 |
| 2016/0252607 A1* | 9/2016 | Saboo | G01S 7/415 342/107 |
| 2016/0284213 A1* | 9/2016 | Cao | G01S 7/415 |
| 2018/0313950 A1* | 11/2018 | Mohamadi | G01S 13/0209 |
| 2019/0195989 A1* | 6/2019 | Childs | G01S 13/345 |

OTHER PUBLICATIONS

Wang et al., "A Hybrid FMCW-Interferometry Radar for Indoor Precise Positioning and Versatile Life Activity Monitoring", IEEE Transactions on Microwave Theory and Techniques, vol. 62, Issue 11, pp. 2812-2822, Nov. 2014.
Peng et al., "A Portable FMCW Interferometry Radar with Programmable Low-IF Architecture for Localization, ISAR Imaging, and Vital Sign Tracking", IEEE Transactions on Microwave Theory and Techniques vol. 65, Issue 4, pp. 1334-1344, Apr. 2017.
Mercuri et al., "Frequency-Tracking CW Doppler Radar Solving Small-Angle Approximation and Null Point Issues in Non-Contact Vital Signs Monitoring", IEEE Transactions on Biomedical Circits and Systems vol. 11, Issue 3, pp. 671-680, Jun. 1, 2017.
Extended European Search Report dated Jan. 18, 2018 for Application No. 17179826.7.

* cited by examiner

Peaks Detection and Treshold

Draft Path Matrix Building

METHOD AND A SYSTEM FOR LOCALIZATION AND MONITORING OF LIVING BEING TARGETS

CROSS-REFERENCE TO RELATED APPLICATIONS

This application claims priority to and the benefit of European Patent Application No. 17179826.7, filed on Jul. 5, 2017, and published as EP 3425419 A1 on Jan. 9, 2019, the disclosure of which is incorporated herein by reference in its entirety.

TECHNICAL FIELD

The present inventive concept relates to a method and a system for localization and monitoring of living being targets. In particular, the present inventive concept relates to radar-based technique for localization and monitoring of targets, including transmitting a radio frequency waveform and receiving a reflected waveform.

BACKGROUND

In recent year, contactless health monitoring has become an increasingly hot topic. For that reason, radar techniques are of high interest as it offers contactless monitoring. Radar techniques have been investigated e.g. for vital signs monitoring, fall detection, localization, etc.

The radar techniques may utilize a Doppler shift that is caused by mechanical movements of heart and chest (lungs) in order to determine vital signs. Also, a Doppler shift may be used for determining speed of a target, which could be used e.g. for distinguishing normal movements from falls, such that fall detection may be performed.

However, performing contactless health monitoring using radar techniques in a real-life environment is very difficult. Reflected signals from a target need to be differentiated from reflected signals from other objects, such as stationary objects, in the environment. Also, if multiple targets are present, the reflected signals from different targets need to be differentiated from each other. Furthermore, determining a mechanical movement of heart and chest, to determine vital signs, may be impossible for a target which is moving through the environment.

In Z. Peng et al, "A Portable FMCW Interferometry Radar With Programmable Low-IF Architecture for Localization, ISAR Imaging, and Vital Sign Tracking", IEEE Transactions on Microwave Theory and Techniques, vol. 65, no. 4, pp. 1334-1344, 2016, a sensor is disclosed which incorporates frequency-modulated continuous wave (FMCW) and interferometry (Doppler) modes, which enables the system to obtain both absolute range information and tiny vital signs (i.e. respiration and heartbeat) of human targets. For the interferometry mode, a low-intermediate-frequency modulation method is implemented to avoid the slow vital signs from being distorted by high-pass filter. Two-dimensional scanning in a complex environment revealed that the proposed radar was able to differentiate human targets from other objects. Moreover, inverse synthetic aperture radar (ISAR) images were used to isolate human targets from surrounding clutter. However, the ISAR images constitute isolated images of moving target positions at a specific moment in time and, in order to track a target, it is required to compute a plurality of ISAR images and identify the target in each of the ISAR images. Hence, tracking of a target is complicated. Further, it is required to change mode of the sensor if vital signs are to be determined, which implies that tracking and determination of vital signs may not be combined.

SUMMARY

It is an object of the present inventive concept to enable tracking of targets in a real-life environment. It is another object of the present inventive concept to enable differentiating targets from stationary objects in the environment. It is a further object of the present inventive concept to enable monitoring of further characteristics of targets, such as vital signs monitoring or fall detection.

These and other objects of the present inventive concept are at least partly met by the invention as defined in the independent claims. Preferred embodiments are set out in the dependent claims.

According to a first aspect, there is provided a method for localization and monitoring of living being targets in an environment, the method comprising: transmitting a sequence of radio frequency waveforms in the environment from a transmitter, each of said radio frequency waveforms being a continuous-wave waveform modulated in frequency and/or phase; detecting a sequence of reflected waveforms, wherein each reflected waveform comprises a contribution of the transmitted waveform being reflected by a target and Doppler-shifted due to a movement of the target, forming a sequence of waveform transforms, wherein each waveform transform is based on a single waveform in the sequence of reflected waveforms, and wherein the waveform transform comprises discretized information in a plurality of range bins, and wherein the information in a single range bin corresponds to reflections occurring at a specific sector in the environment in relation to the transmitter; analyzing information for a single specific sector in a sub-sequence of the sequence of waveform transforms, and determining movement of a target in the specific sector based on the waveform transform information for that specific sector during a time period corresponding to the sub-sequence.

The method enables analysis of movements of targets, such that multiple targets in the environment may be tracked. The analysis of information for a single sector in a sub-sequence of waveform transforms enables determination of a movement in the single sector during the time period corresponding to the sub-sequence. By means of performing such analysis for each specific sector, movements in each sector may be determined. Further, by performing analysis for a multitude of consecutive sub-sequences, movements of targets may be tracked for the time period corresponding to the sequence of transmitted waveforms.

The method allows determining a movement in the single specific sector. According to an embodiment, a single constant speed of movement is assigned to the specific sector for the time period corresponding to the sub-sequence. Hence, a dominant movement during the time period corresponding to the sub-sequence may be determined and used for further analysis. This enables extracting relevant information from the detected reflected waveforms such that further analysis of the environment in order to perform tracking of objects is simplified.

A size of each of the specific sectors and a length of a time period of a transmitted single radio frequency waveform may be such that a target may be considered to be static during a duration of the single frequency waveform. In particular, the target will not to be able to move from one sector to another sector during the time period. For instance, the time period may be in the order of 100 µs, such that a human target may be able to only move fractions of a mm during the time period. According to an embodiment, the analyzing information for a single specific sector in a single waveform of the sequence of waveform transforms is based on a target being considered not to move between sectors during a time period of a single transmitted radio frequency waveform. In other words, a frequency shift between reflected and transmitted signals corresponding to a single reflected waveform may be transferred to a corresponding distance to a moving target. This implies that an ambiguity of contribution of range to a target and velocity of a target in causing a frequency contribution may be eliminated in the analysis of a single waveform.

A speed of the target may be determined based on a sequence of phase changes caused by the target in a sub-sequence of the sequence of transmitted radio frequency waveforms. The sub-sequence may span over a time period that is so short that the moving target may not be able to move over several sectors during the time period. At most, the human target may move from one sector to an adjacent sector, e.g. if the human target moves from an edge of one sector into an adjacent sector. The phase change occurring for a single sector in a sub-sequence of the sequence of transmitted radio frequency waveforms may thus be used for determining a speed of the target.

The tracking of targets may allow determining a position of each target in the environment during the transmitting of the sequence of radio frequency waveforms. Thanks to tracking of targets, it is possible to know that a target is in a specific sector (or specific sectors, as the target may occupy more than one sector), even if the target stops moving and stays within the sector. Thus, if a target stops and maintains a position within a specific sector for a period of time, vital signs of the target may be extracted, while no disturbances of the determination of vital signs due to the target moving between sectors occurs. Hence, the determining of movements of a target within a sector may also comprise determining vital signs, such as respiration and heartbeat, of the target.

The transmitted radio frequency waveform may be a modulated continuous-wave waveform, wherein it is possible to differentiate between consecutive waveforms. There may be a time gap between an end of a waveform and a start of the next waveform. However, as an alternative, there is no gap, but rather a waveform may be transmitted immediately after the end of a previous waveform.

The waveform may be a frequency-modulated continuous wave (FMCW), a step-frequency continuous wave (SFCW) or a phase-modulated continuous wave (PMCW). In at least some embodiments, the waveform may be considered a single modulated pulse.

The waveform transform may be any type of transform that allows extracting information from the detected reflected waveform into a plurality of discretized range bins. For example, the waveform transform may be achieved as a digital Fourier transform, such as fast Fourier transform (FFT). However, if a PMCW waveform is transmitted, the detected reflected waveform may be compared to a set of correlators for extracting the information in a plurality of discretized range bins.

According to an embodiment, said waveform transforms are Fourier transforms, and a range bin corresponds to a single frequency range in the Fourier transform. The Fourier transform may be divided into a plurality of frequency ranges, which may define range bins and, hence, sectors in the environment. Thus, contribution of each sector in the detected reflected waveform may be isolated allowing movements in each sector to be separately determined.

It should be realized that the sectors may be defined in relation to a transceiver comprising a transmitter and a receiver. A transmitter and a receiver may alternatively be arranged in different positions, which implies that a sector may be differently related to the transmitter and the receiver. However, it should be realized that the relation to the transmitter has a fixed offset to the relation to the receiver, so even if sectors would be defined in relation to the receiver, the sectors also have a fixed, defined relation to the transmitter.

According to an embodiment, said analyzing comprises determining a peak frequency of a phase change in the sub-sequence for the specific sector, wherein the peak frequency is indicative of a speed of a target in the specific sector during the time period.

If the peak frequency is at DC, there is no moving target in the range bin. On the other hand, a moving target will cause a phase change that has a dominant peak which is not at DC. Thus, by analyzing the peak frequency of the phase change, a movement of a target in the specific sector may be efficiently determined.

The speed of the target may be determined based on the detected peak frequency and a representation of speed of targets within specific sectors of the environment may be formed, wherein each sector (or range bin) is assigned a speed corresponding to the determined peak frequency for the duration of the sub-sequence. This implies that a representation of speed of movements may be produced, which may enable processing of detected reflected waveforms in an efficient manner in order to allow for tracking of targets.

According to an embodiment, the method further comprises combining the sequence of Fourier transforms with speed information in the specific sector in the environment to obtain a combined measure of speed and magnitude of reflection from targets in the specific sector.

If a speed is determined based on the determined peak frequency, such a single speed value may be assigned to each specific sector and a number of time instances, wherein each time instance corresponds to a single waveform in a number of consecutive waveforms used for determining the phase change and hence the speed. Hence, a combination of speed and magnitude of reflection may be easily formed, e.g. for each specific sector in each time instance a multiplication of the speed and magnitude of reflection may be calculated. This combined measure allows differentiating moving targets from stationary objects (which will score a low value on the speed).

According to an embodiment, the method further comprises comparing combined measures of speed and magnitude of reflection to at least one threshold for identifying targets in the environment. The comparison to a threshold allows removing detected reflections from stationary objects, which should form measures below the at least one threshold.

According to an embodiment, a draft path of a target in the environment during a time period corresponding to the sequence of radio frequency waveforms is based on the combined measures of speed and magnitude of reflection. The method may further comprise tracking a path of a target by analyzing selected potential positions of the target based on the combined measure at a time instance corresponding to a single waveform in relation to a determined position of the target at a previous time instance corresponding to a previous single waveform in the sequence of reflected waveforms.

Based on the comparison of the combined measures of speed and magnitude of reflection to at least one threshold, a binary representation whether a moving target may be present within each specific sector at each time instance corresponding to a single waveform (or a number of consecutive waveforms) may be formed. The binary representation may thus represent potential positions of targets in each time instance. It may be desired that the threshold is set so as to ensure that moving targets are not filtered away in the analysis. Hence, some residues of reflections from stationary objects may still be present after comparison of the combined measures of speed and magnitude of reflection to at least one threshold, especially at times when a moving target passes between a transmitter/receiver and the stationary object. Such residues may be removed by analyzing selected potential positions of the target based on determined positions in a previous time instance. The path of the target may be established in this manner, while isolated residues of reflections from stationary objects may be removed.

It should be realized that paths of multiple targets may be simultaneously determined, wherein selected potential positions for each target that is tracked may be analyzed such that the movements of the paths of multiple targets may be determined while still removing residues of reflections from stationary objects.

According to an embodiment, the tracked path of a target is combined with speed information in the specific sector in the environment to obtain a speed profile of the target during a time period corresponding to the sequence of radio frequency waveforms. Once the tracked path has been determined, it may be combined with the speed information such that both speed and position of the target for a time period corresponding to the sequence of radio frequency waveforms may be obtained. The tracked path could be represented as a binary matrix, wherein a presence of a target in a specific sector at a time instance is represented as a "1". Thus, the binary matrix may be multiplied with a matrix comprising speed information in each specific sector at each time instance in order to provide a speed profile of a target along a tracked path.

According to an embodiment, the method further comprises forming a number of groups of sub-sequences in the sequence of Fourier transforms, and performing said analyzing of information and determining of movement of a target for each group in said number of groups of sub-sequences. The number of groups of sub-sequences may form multiple consecutive sub-sequences, such that all of the Fourier transforms in the sequence are analyzed. This determining of movements of a target within the groups of sub-sequences may allow tracking of the target through the sub-sequences.

According to an embodiment, a length of a sub-sequence is selected based on a desired resolution of speed of targets. The amount of processing of the detected reflected waveforms is dependent on the length of a sub-sequence, as speed of movements is determined for each sub-sequence. Hence, by setting a desired speed resolution, the amount of processing required may be limited. If a wavelength of the transmitted waveform is in the GHz spectrum, the length of the sub-sequence may be several ms, while enabling determining movements with a speed resolution of fractions of 1 m/s.

According to an embodiment, analysis is based on a pre-defined number of detected reflected waveforms in the sequence, and the method further comprises refreshing analysis of movements of target based on each sequence of a pre-defined number of detected reflected waveforms. Hence, tracking of targets may be performed during the sequence of pre-defined number of detected reflected waveforms. Then, a new set of a sequence of the pre-defined number of detected reflected waveforms may be acquired in order to perform a tracking of targets for another time period. Knowledge of positions of targets at the end of a sequence may be used as initial values in a subsequent sequence. Thus, if a target does not move between different sectors during a sequence of detected reflected waveforms, the position of the target may be known based on a previous sequence. This also implies that the sequence may be used for vital signs monitoring based on knowledge that a person is present in a sector and using the sequence to detect slow movements corresponding to heartbeat and/or respiration.

According to an embodiment, the sequence of reflected waveforms is used for vital signs monitoring based on a target that remains in a specific sector during at least a sub-sequence of the sequence of reflected waveforms. The detected reflected waveforms may hence include information of Doppler shifts caused by mechanical movements of the heart and chest. The mechanical movements have a frequency corresponding to heart rate and respiratory rate, which may be extracted from the detected reflected waveforms. Thus, the sequence of reflected waveforms may be used both for tracking targets and for detecting or monitoring vital signs of targets.

The specific sector may be defined to be larger than the movement caused by the mechanical movements of the heart and chest. Thus, even though the target may occupy several sectors, the mechanical movement may occur within one sector, which is helpful in extracting the vital signs information. For instance, the mechanical displacement due to respiration may typically be 0.8 mm, whereas a size of a sector may extend over tens of cm.

According to an embodiment, said analyzing of information and said determining of a movement is performed for each single range bin in the waveform transforms corresponding to reflections occurring at different specific sectors in the environment.

This implies that movements within each sector of the environment may be determined. It should however be realized that some sectors may be disregarded, such that the analysis is not necessarily performed for each possible sector in the environment from which reflections may be received. For instance, walls, floors and ceilings may be defined such that sectors in such structures are not considered. Also, sectors in which no movement is expected, such as very close to a ceiling, may also be disregarded.

According to an embodiment, the method further comprises using more than one transmitter or using multiple-input multiple-output (MIMO) or beamforming transmission and combining detected sequences of reflected waveforms for including angular information in definition of sectors of the environment.

If a single transmitter with no angular selection of transmission is used, the environment may be divided into circular sectors (or sectors extending along an arc), each representing a common distance from the transmitter. Thus, it may not be possible to distinguish between targets at the same distance from the transmitter, but at different angles. However, if more than one transmitter differently positioned in the environment and/or MIMO and/or beamforming is used, it may be possible to differentiate between targets at different angles. Hence, the sectors may be defined according to a desired geometry, e.g. forming right parallelepipeds, such as cubes, in the environment.

The method may also comprise using a wireless radar sensor network based on a plurality of transmitters and/or receivers for including angular information in definition of sectors of the environment.

According to an embodiment, the method may further comprise analyzing determined movement of a target for detecting falling of the target. As the movement of a target through the environment may be tracked, the movement may also be analyzed in order to determine abnormal movements corresponding to falls. Thus, falling of the target may be detected, which may be useful in determining accidents, e.g. in elderly care.

A fall may be detected by the speed of the target increasing as the fall progresses, followed by an abrupt stop when the target hits the ground. However, the method of determining both speeds and positions of targets may be especially useful in detection also of "soft" falls, wherein a target slowly and smoothly falls to the ground. Thanks to the knowledge of both position and speed, the fall detection need not be based merely on analysis of changes in speeds of the target, but also information of positions of the target may be used to determine that the target has fallen to the ground.

According to an embodiment, the method further comprises determining an alert situation based on said determining of movement of a target. For instance, detection of a fall of a target may correspond to an alert situation, but other events may also be considered as alert situations, e.g. if vital signs monitoring produces abnormal values. The method may thus comprise determining of alert situations which may allow triggering of an alert that may be transmitted to an external monitoring unit, for allowing summoning for help to the target in the monitored environment.

According to a second aspect, there is provided a system for localization and monitoring of living being targets in an environment, the system comprising: a transmitter for transmitting a sequence of radio frequency waveforms in the environment, each of said radio frequency waveforms being a continuous-wave waveform modulated in frequency and/or phase; a receiver for detecting a sequence of reflected waveforms, wherein each reflected waveform comprises a contribution of the transmitted waveform being reflected by a target and Doppler-shifted due to a movement of the target, and a processor for processing the detected sequence of reflected waveforms, said processor being configured to: form a sequence of waveform transforms, wherein each waveform transform is based on a single waveform in the sequence of reflected waveforms, and wherein the waveform transform comprises discretized information in a plurality of range bins, and wherein the information in a single range bin corresponds to reflections occurring at a specific sector in the environment in relation to the transmitter; analyze information for a single specific sector in a sub-sequence of the sequence of waveform transforms, and determine movement of a target in the specific sector based on the waveform transform information for that specific sector during a time period corresponding to the sub-sequence.

Effects and features of this second aspect are largely analogous to those described above in connection with the first aspect. Embodiments mentioned in relation to the first aspect are largely compatible with the second aspect.

The system thus may be set up for monitoring an environment such that targets may be localized and monitored in the environment. The system may be used for autonomous monitoring and may further be set up to transmit or create alerts when an event that may need manual handling is detected.

According to a third aspect, there is provided a computing device for localization and monitoring of living being targets in an environment, the computing device comprising a processor for receiving and processing a detected sequence of reflected waveforms, said processor being configured to: form a sequence of waveform transforms, wherein each waveform transform is based on a single waveform in the sequence of reflected waveforms, and wherein the waveform transform comprises discretized information in a plurality of range bins, and wherein the information in a single range bin corresponds to reflections occurring at a specific sector in an environment in relation to a transmitter; analyze information for a single specific sector in a sub-sequence of the sequence of waveform transforms, and determine movement of a target in the specific sector based on the waveform transform information for that specific sector during a time period corresponding to the sub-sequence.

According to a fourth aspect, there is provided a computer program product comprising a computer-readable medium with computer-readable instructions such that when executed on a processor the computer program will cause the processor to process a detected sequence of reflected waveforms in accordance with the method of the first aspect.

Effects and features of these third and fourth aspect are largely analogous to those described above in connection with the first and second aspects. Embodiments mentioned in relation to the first and second aspects are largely compatible with the third and fourth aspects.

The processor may be executing a computer program product or may be configured in any other manner, such as by hardware or firmware configuration, for implementing the processing performed by the processor. The processor may be able to process the detected sequence of waveform transforms for monitoring of living being targets in an environment. The computing device with the processor may be remotely arranged from the transmitter/receiver or integrated in a common housing with the transmitter and/or receiver, to process the detected information. Thus, the computing device may be arranged in a location most convenient for performing the processing of the detected sequence of reflected waveforms.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION

A method for localization and monitoring of living being targets in an environment is provided. The method uses transmitting of radio frequency waveforms and detecting reflected waveforms, wherein the detected waveforms are analyzed in order to locate targets and also monitor movements of targets and/or monitor vital signs. Before an embodiment of the method will be described in further detail, some explanations of detected waveforms will be given. The explanations below are mainly provided for a frequency-modulated continuous wave (FMCW) radar, but it should be realized that a step-frequency continuous wave (SFCW) radar or a pulse-modulated continuous wave (PMCW) radar may be used instead.

Figure 1:
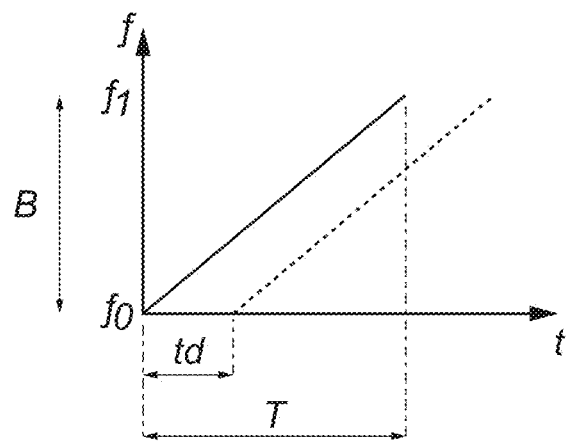
FIG. 1 is a chart illustrating a transmitted waveform and a received reflected waveform.

Referring now to FIG. 1, a linear FMCW radar transmits a waveform, hereinafter called a chirp, wherein an instantaneous transmitting frequency $f_t$ of the chirp varies linearly over time (as illustrated by the solid line 102 in FIG. 1). The variation of the frequency can be expressed as:

$$f_t = f_0 + \frac{B}{T}t \quad (1)$$

where $f_0$ is an initial frequency of the chirp, B is a total band of the waveform, while T is a duration of the chirp. The relation B/T may be called a sweeping rate of the waveform. The corresponding phase of the waveform is:

$$\phi = 2\pi \int_0^t f_t dt = 2\pi\left(f_0 t + \frac{B}{2T}t^2\right) \quad (2)$$

A transmitted waveform $T_s(t)$ can be expressed as:

$$T_s(t) = A\sin\left[2\pi\left(f_0 t + \frac{B}{2T}t^2\right)\right] \quad (3)$$

where A is an amplitude of the transmitted waveform.

The transmitted waveform is reflected by a target at a distance $D_0$ from the transmitter. Assuming a stationary target, the reflected waveform R(t) (as illustrated by the dashed line in FIG. 1) can be expressed as:

$$R(t) = B(t)\sin\left[2\pi\left(f_0(t-t_d) + \frac{B}{2T}(t-t_d)^2\right)\right] \quad (4)$$

where B(t) is a term dependent on reflection of the transmitted waveform by the target and also dependent on path loss and attenuation, and $$t_d = \frac{2D_0}{c} \quad (5)$$

where c is speed of an electromagnetic wave in a medium of the environment (typically air).

The transmitted waveform $T_s(t)$ and a received reflected waveform R(t) may be mixed and the mixed signal may be input to a low-pass filter. The resulting signal may be called a beat signal BS and can be expressed as:

$$BS(t) = C(t)\cos\left[2\pi\left(\frac{2BD_0}{cT}t + \frac{2f_0 D_0}{c} + \frac{B}{2T}\left(\frac{2D_0}{c}\right)^2\right)\right] \quad (6)$$

where C(t) is a term dependent on the amplitude A of the transmitted signal and the reflection B(t) of the signal by the target. In equation (6), only the first term of the cosine function is time-varying term and is called beat frequency $f_b$. The other two terms of the expression in equation (6) are phase components. The squared term is essentially zero, especially for short-distances, which means that equation (6) can be expressed as:

$$BS(t) \approx C(t)\cos\left[2\pi\left(\frac{2BD_0}{cT}t + \frac{2f_0 D_0}{c}\right)\right] \quad (7)$$

This implies that for a static target, a resulting baseband signal is a sinusoidal waveform whose frequency (beat frequency), depending on the target's absolute distance, is $2BD_0/cT$ and the initial phase is $2f_0 D_0/c$. The beat frequency may be used to determine an absolute distance to the target while the initial phase may provide Doppler information that may be used for determining a movement of the target. Although the initial phase depends also on the range $D_0$, this information cannot be used to determine the absolute distance to the target, while it can be used to determine the Doppler information, as in a pure continuous wave radar. In fact, $2f_0 D_0/c$ is a periodic of $2\pi$, meaning that a maximum unambiguous range will be $D_0 = c/(2f_0)$, which is a few millimeters/centimeters at microwave frequencies and, hence, a distance cannot be unambiguously determined in a real-life environment.

In case of a moving target at speed v, an absolute distance to the target varies with time and becomes $D=D_0+vt$, and the beat signal can then be expressed as:

$$BS(t) = C(t)\cos\left[2\pi\left(\frac{2BD_0 t}{cT}\left(1-\frac{2v}{c}\right)+ \frac{2f_0 vt}{c} + \frac{2Bvt^2}{c}\left(1-\frac{v}{c}\right) + \frac{2D_0}{c}\left(f_0 - \frac{BD_0}{cT}\right)\right)\right] \quad (8)$$

This expression comprises ambiguities for differentiating between a distance to the moving target and a velocity of the moving target. In fact, the distance to a target is calculated from the received frequency shift. In the case of moving target, there will also be a frequency shift because of the Doppler effect. This makes it hard to say if the shift is caused by the range or the velocity. However, considering speeds of human targets, if the chip duration T is made sufficiently short, it can be assumed that all the instantaneous frequencies of the chirp are reflected by the target at the same distance $D_0$. This means that during T the target speed can be considered to be essentially 0 m/s, meaning the target is frozen at $D_0$.

This means that equation (8) can be approximated as equation (7) for the time duration of the chirp. Hence, by using an assumption that the target may be considered to be located at the distance $D_0$ during the duration of the chirp, the location of the target may be accurately determined.

To further reduce the range/velocity ambiguities, the FMCW signal may comprise a linear up-sweep and a linear down-sweep in frequency. It is, in fact, observed that in the case of Doppler shift, a higher velocity causes greater frequency shift during the up-sweep and smaller frequency shift during the down-sweep. Thus, by exploiting both the up-sweep and the down-sweep, the Doppler shift can be separated from the range-induced shift, which is the same for both the up-sweep and the down-sweep. In this way, the FMCW radar is capable of both range and velocity measurements, even if the distance to the target cannot be assumed to be constant during the chirp duration T. The up-sweep and the down-sweep should be symmetrical. The technique of using an up-sweep and a down-sweep works well if the target is moving at constant speed during the waveform transmission, like in automotive applications. However, this may not always be assumed for movements by human targets. For that reason, it may be advantageous to use the assumption that the target may be considered to be located at the distance $D_0$ during the duration of the chirp.

Figure 2:
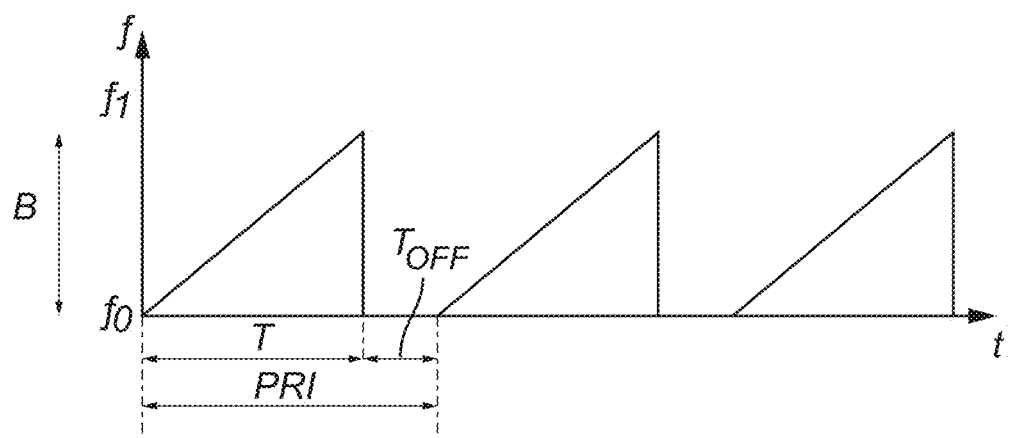
FIG. 2 is a chart illustrating a series of transmitted waveforms.
Figure 3:
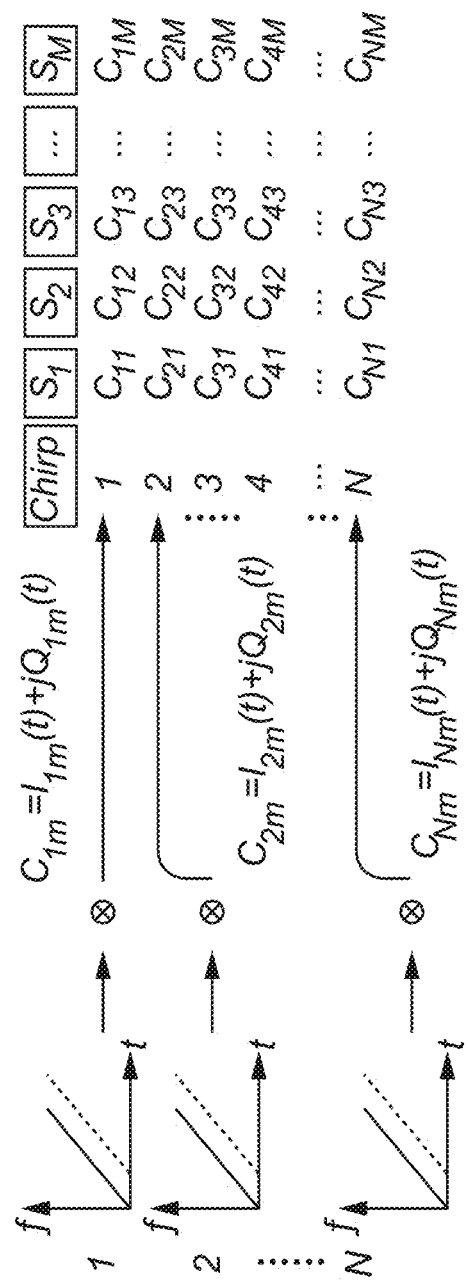
FIG. 3 is a scheme illustrating forming samples based on baseband signals of the received and transmitted waveforms.
Figure 4:
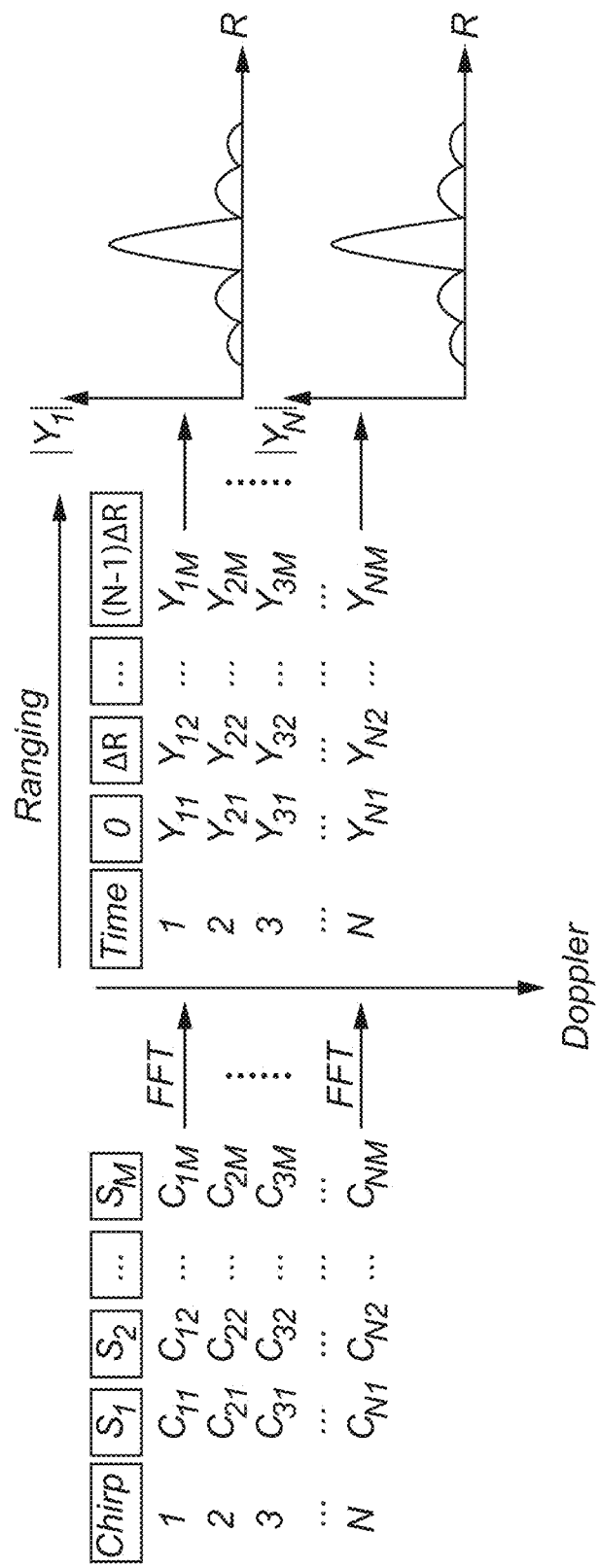
FIG. 4 is a scheme illustrating forming of waveform transforms providing indications of presence of targets at different sectors (range bins).

Referring now to FIGS. 2-4, processing of a detected reflected waveform will be further described, with reference to a transmitted FMCW waveform. As illustrated in FIG. 2, a series of N chirps are transmitted. The duration of a waveform is T and is followed by an interval $T_{OFF}$ before the next chirp is transmitted. The interval $T_{OFF}$ may be 0 seconds, i.e. a chirp may be transmitted immediately following an end of the previous chirp, or any values depending on the application and requirements. For example, it can be used to provide a duty cycle to fit spectral masks of the transmitted. A pulse repetition interval PRI is thus given by $T+T_{OFF}$.

The baseband signal (beat signal) produced based on each detected chirp may be digitized to produce M samples. For a quadrature receiver, the M IQ samples are related to produce M complex samples while, for a single-channel receiver, real samples are produced. M depends on a sampling rate of an analog-to-digital converter. The N·M samples produced by N beat signals may be arranged in a data matrix as illustrated in FIG. 3, where columns $S_1$-$S_M$ denotes the M samples and values $C_{ij}$ correspond to sample j for chirp i.

Each set of M samples (for each chirp) may be transformed such that a waveform transform based on the detected reflected waveform (mixed with the transmitted waveform) is generated. For an FMCW waveform or a SFCW waveform, a Fourier transform may be formed, based on a fast Fourier transform (FFT), as a digitized representation of the baseband signal has been created.

The FFT is performed for each row of the data matrix illustrated in FIG. 3, such that, for each chirp, a waveform transform is generated that comprises information of distance to targets. As demonstrated by equation (7), each target produces a beat frequency $f_b$ which is proportional to the distance (or range) as:

$$R_0 = \frac{cT}{2B} f_b \quad (9)$$

As illustrated in FIG. 4, for each time $t_1$-$t_N$ corresponding to a PRI, a waveform transform is generated which determines values for different frequencies. As M samples have been collected for the baseband signal, the frequency representation of the waveform will also be resolved into M samples. Hence, at each time instance $t_i$, M values $Y_{ij}$ are generated. As illustrated by graphs in FIG. 4, each waveform transform may provide an indication of target positions (range R to target) as an absolute value of Y for the range will be high if a target is present in the range.

This implies that at each time interval corresponding to a PRI, new absolute distances to targets are estimated. The range resolution $\Delta R$ depends on the chirp bandwidth B as $\Delta R=c/(2B)$. Thus, depending on its position, the target will be localized to a sector in the environment corresponding to a range bin determined by the discrete FFT values, in which the beat frequency generated by the target will be resolved.

The result of the FFT for each row of size M is a complex value of size M by which it is possible to extract magnitude and phase information. This implies that when the FFT transform is applied over N rows (namely N chirps), there is Doppler information along each column of the matrix (corresponding to FFT values for a specific range bin over time). For example, if the target is at a range $R_0$ (for example $R_0$=10.2*$\Delta R$), it will be located to the nearest resolution in the range profile (for example 10*$\Delta R$). The column corresponding to 10*$\Delta R$ may then be used for extracting Doppler information by which vital signs and speed information of the target can be determined. The number of chirps N that is needed for drawing conclusions based on the Doppler information may depend on the application (e.g. a speed of the movement that is to be detected), such that different number of chirps may be needed for detecting speed of movement of a target through the environment, or for vital signs monitoring.

For example, the speed of a target moving through the environment may be determined measuring the Doppler frequency $f_d$ based on a change in phase $\phi$ as:

$$\frac{\partial \phi}{\partial t} = 2\pi f_d = \frac{4\pi}{\lambda_0} \frac{\partial R_0}{\partial t} = \frac{4\pi}{\lambda} v(t) \quad (10)$$

$$v(t) = \frac{\lambda_0}{2} f_d = \frac{c}{2 f_0} f_d \quad (11)$$

where $\lambda_0$ is a wavelength corresponding to the initial frequency of the chirp.

Figure 5:
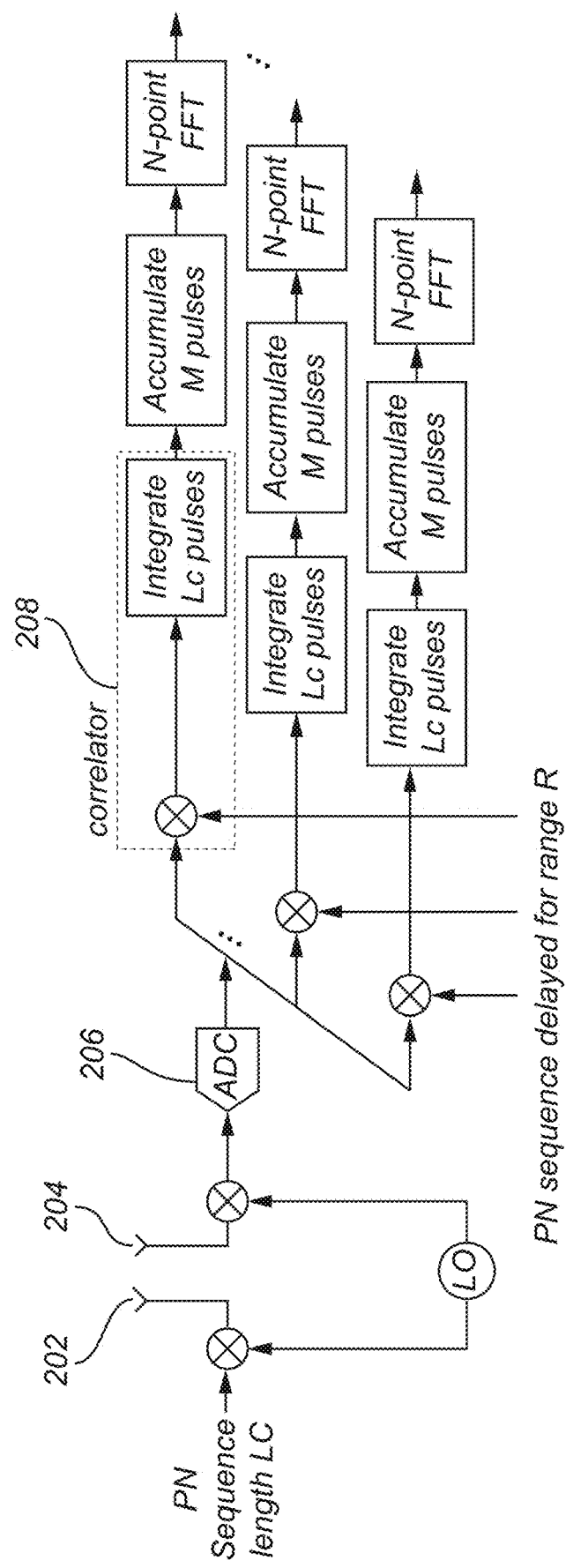
FIG. 5 is a schematic view of a set-up for processing of reflected waveforms based on a transmitted phase-modulated continuous wave waveform.

The previous description is valid for transmission of FMCW and SFCW waveforms. However, if a PMCW waveform is transmitted, a Fourier transform may not be created in order to arrange information in range bins. For the PMCW, the range profile may be calculated in a different way in order to associate the detected reflected waveform with respective range bins. As illustrated in FIG. 5, a transmitter 202 may transmit a PMCW waveform. A reflected waveform is received by a receiver 204 and mixed with the transmitted waveform in order to generate a baseband signal. The baseband signal is digitized in an analog-to-digital converter 206. After digitization of the baseband signal, the baseband signal may be combined with a bank of correlators 208, wherein each correlator 208 mixes the baseband signal with a respective delay of the phase-modulating sequence. The mixed signal is integrated over a length of the phase-modulated waveform and is accumulated for the M samples of the baseband signal. Thus, each correlator 208 may create a value corresponding to reflection of the transmitted signal at a respective range, such that a range profile may be formed.

Groups of N·M samples (each group being produced by N beat signals detected in $T_d$ seconds) may be arranged in a data matrix as illustrated in FIG. 3 and processed. Therefore, this data matrix consists of groups of N·M submatrices and has dimension G·N×M, where G is the number of groups considered. Each row is produced after PRI seconds, meaning that a maximum unambiguous speed is:

$$v_{max} = \frac{\lambda_0}{4PRI} \quad (12)$$

The time $T_d$ in which a speed of a movement is evaluated may be selected taking into account a desired speed resolution $\Delta v$ which is given as:

$$\Delta v = \frac{\lambda_0}{2T_d} \quad (13)$$

Figure 6:
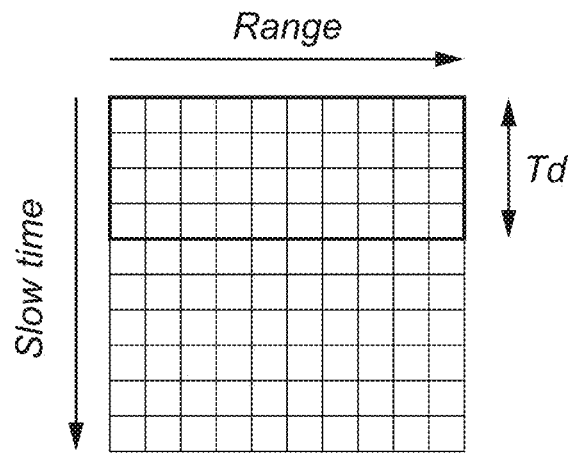
FIG. 6 is a scheme illustrating sub-sequences in a range profile for determining speeds of targets in an environment.

As illustrated in FIG. 6, each N·M submatrix, corresponding to a $T_d$ interval, may be initially processed independently in order to estimate a speed profile of a target. First, the range profile may be determined as described above. After the waveforms have thus been transformed to arrange information from the detected waveforms in relation to range bins corresponding to reflections occurring at respective specific sectors in the environment, Doppler information for each range bin (i.e., for each column) may be estimated by extracting the phase information. For example, if at a certain range bin there is a target moving toward the transmitter/receiver with constant speed, the phase over the column corresponding to that range bin will change with a ramp trend. On the other hand, if there is no target in the range bin, the phase will experience a small and random change due to noise.

Figure 7:
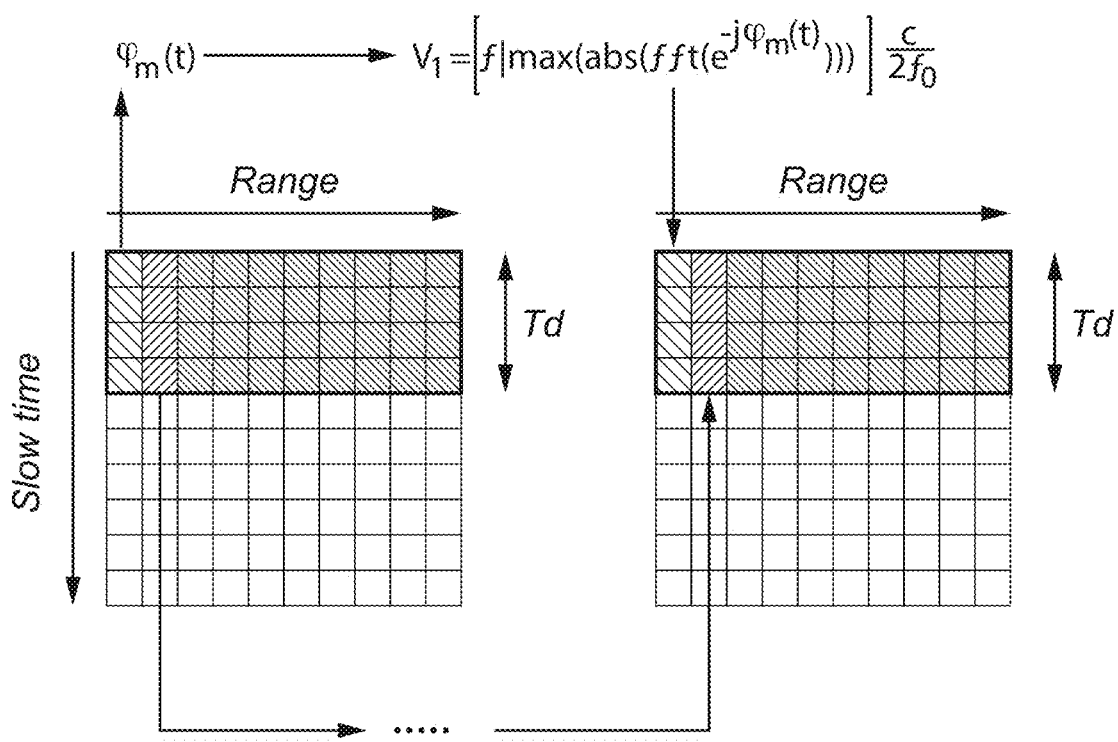
FIG. 7 is a scheme illustrating calculations of speeds of targets.

As illustrated in FIG. 7, for each column m, a signal can be generated as:

$$y_m(t) = e^{-j\phi_m(t)} \quad (14)$$

A sub-sequence corresponding to a $T_d$ interval of each column, corresponding to reflections from a specific sector in the environment, may now be analyzed. The sub-sequence may be processed by assessing a FFT of the sub-sequence. Frequencies of the sub-sequence may thus be analyzed, and the frequencies may be correlated to speed of movements of a target in the specific sector.

Thus, a peak in a spectrum resulting from the FFT may be determined. The frequency corresponding to the peak may then be used as a representation of a dominant movement in the range bin. The frequency may further be used for determining the speed in that range bin through equation (11). As illustrated in FIG. 7, the speed $v_m$ in the sub-sequence of column m may be determined by:

$$v_m = [f \mid \max(\mathrm{abs}(\mathit{fft}(e^{-j\varphi_m(t)})))] \frac{c}{2f_0} \quad (15)$$

This determined value of the speed may be inserted in each element in the sub-sequence of the m-th column. If in that range bin there is a moving target, it will produce a phase change whose dominant peak in frequency domain is not at DC, otherwise the only peak will be normally centered at DC (corresponding to a zero speed), unless there is a noise component stronger than the phase DC level.

The above procedure may be repeated over time for all G submatrices (each of N·M dimension) of the whole data matrix, such that information of consecutive sub-sequences in the sequence of waveform transforms is analyzed.

Figure 8:
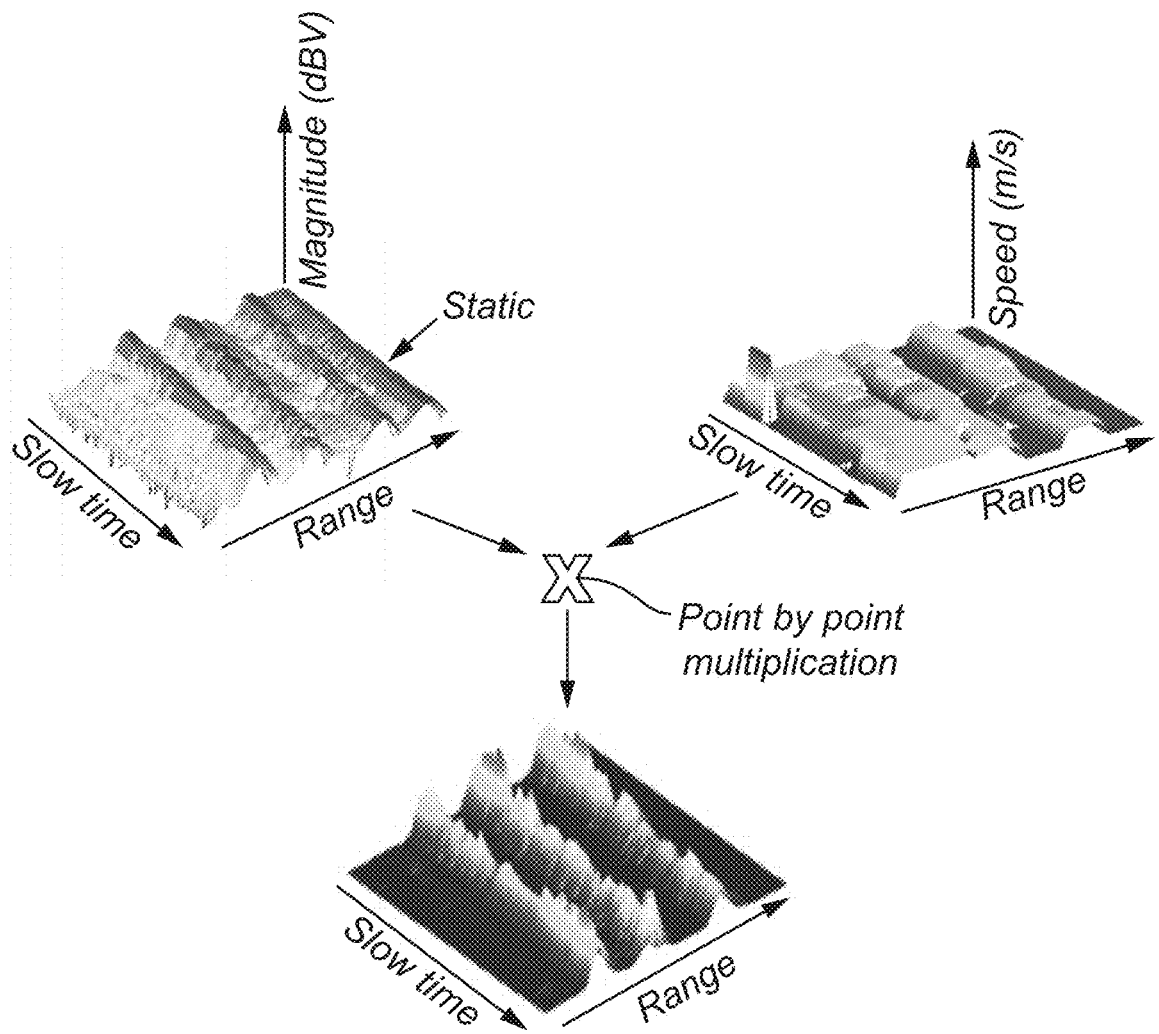
FIG. 8 is a scheme illustrating forming a combined representation of speeds and positions of targets.

The matrix illustrated in FIG. 7 may be called a Speed Matrix as it comprises information of the speed of targets. After the determination of the Speed Matrix, the speed information may be combined with the range profile, e.g. in the form of a Range Profile Matrix illustrated in FIG. 6. As illustrated in FIG. 8, the combination may be formed by matrix multiplication, wherein the elements of the Speed Matrix are multiplied point by point with the magnitudes of the elements of the Range Profile Matrix. This combination may generate a new matrix, which may be called Range Speed Matrix (RSM), whose dimension is G·N×M.

Values of the elements of the Range Speed Matrix has a contribution based on speed of targets in sectors of the environment and a contribution based on magnitude of reflection from the sectors. Thus, a large magnitude of reflection based on a stationary object may still render a small value in the Range Speed Matrix, based on a small or zero speed being determined in the sector. Further, a determined speed in a sector attributable to noise may still render a small value in the Range Speed Matrix, based on the magnitude of reflection being small from that sector.

Figure 9:
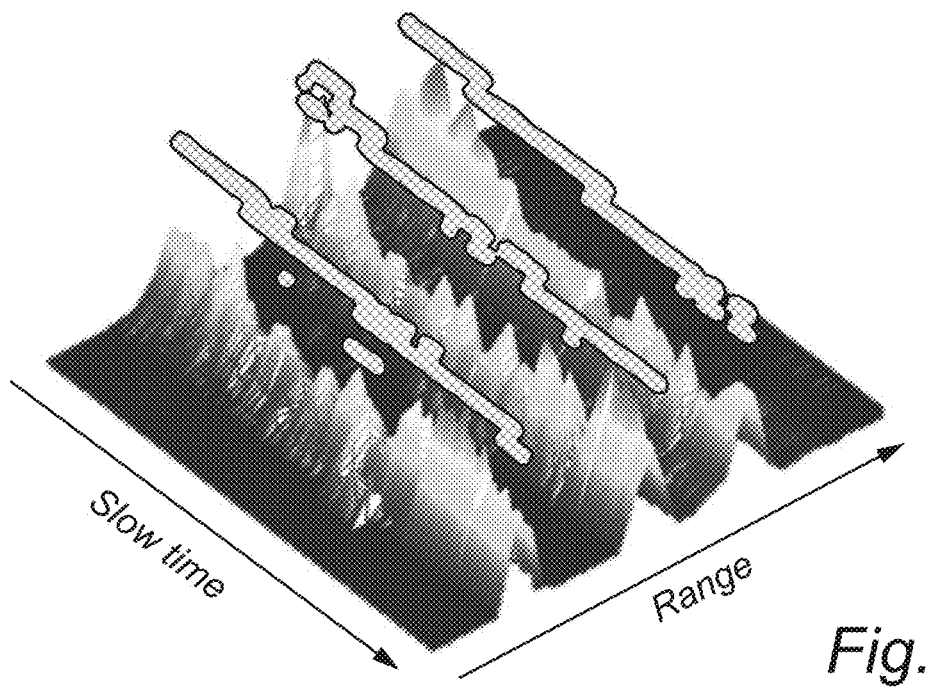
FIG. 9 is a scheme illustrating identifying peaks corresponding to targets.

Thus, the Range Speed Matrix may provide information of positions of moving targets in the environment. The Range Speed Matrix may however still contain residues from static reflectors. For that reason, a peak detection algorithm may be used for every slow time (i.e. time instance corresponding to a single waveform or a number of consecutive waveforms) to find local maxima in the Range Speed Matrix. The local maxima may then be compared to a threshold Thr and only local maxima above the threshold Thr may be maintained in the Range Speed Matrix. After this comparison, the remaining peaks are considered to be targets (illustrated by checkered dots in FIG. 9). The threshold Thr is slow time dependent and may be calculated as:

$$Thr_i = \bar{x}_i + k\sqrt{\frac{1}{M}\sum_{m=1}^{M}[RSM(m,i) - \bar{x}_i]^2} \quad (16)$$

with $$\bar{x}_i = \frac{1}{M}\sum_{m=1}^{M} RSM(m,i) \quad (17)$$

where i=1, 2, . . . is an index over the slow time dimension, and k is a constant that can be tuned to change the sensitivity in detecting a target.

Figure 10:
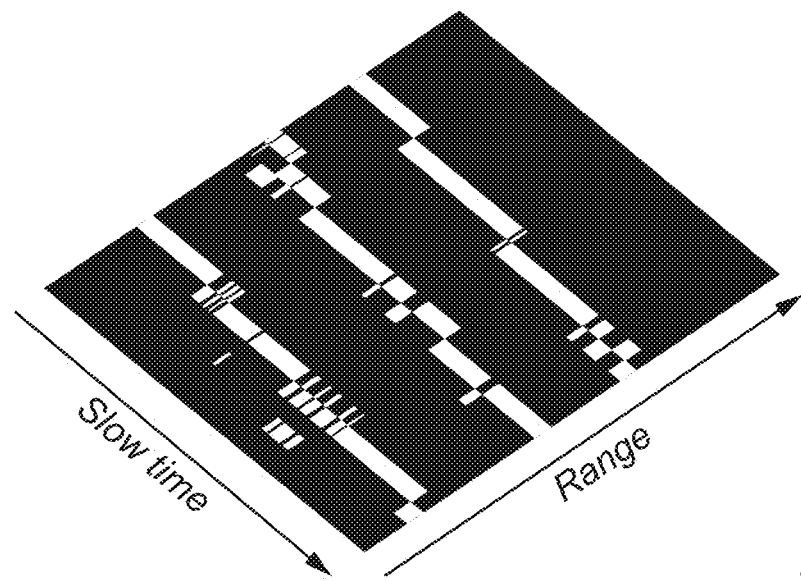
FIG. 10 is a scheme illustrating determination of draft paths of targets through an environment.

After the comparison to a threshold, a rough map of paths of target in the environment over time may be formed. The rough map, illustrated in FIG. 10, may be called a Draft Path Matrix (DPM), and may comprise information of the number of targets and their information about speeds and absolute distances over time. In the Draft Path Matrix, some residues from static reflectors may still be present.

Figure 11:
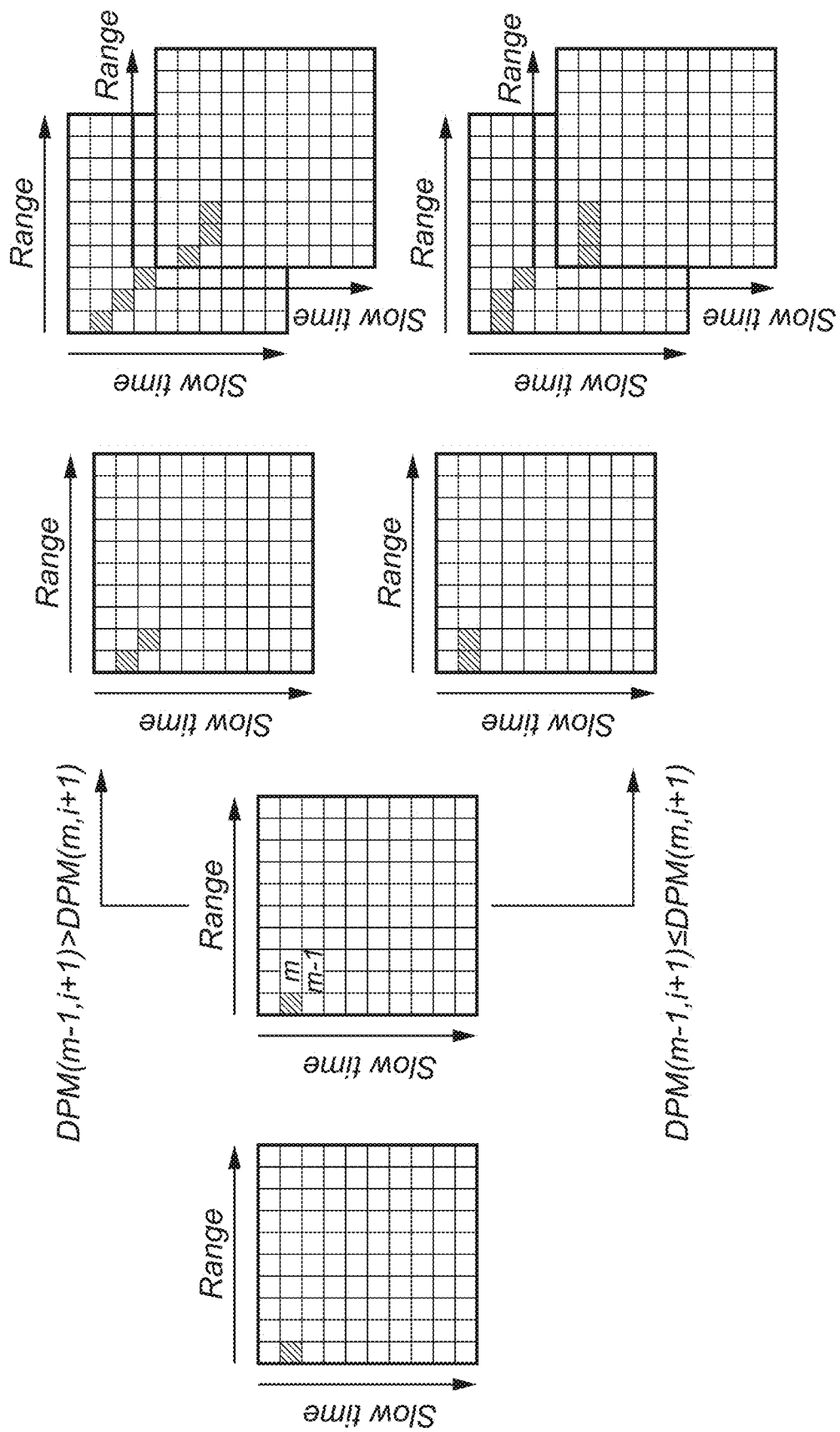
FIG. 11 is a scheme illustrating a tracking algorithm for tracking target paths.

Referring now to FIG. 11, a tracking algorithm may be used based on the Draft Path Matrix in order to determine paths of targets. First, positions of the targets and the speeds of the targets may be determined at the initial time. Then, a tracking algorithm may be used for evaluating properly the targets' paths. The position of the targets is determined for each time instance at a time and the Draft Path Matrix is thus stepped through in order to determine the path of the targets.

For each predicted target, the speed sign is first considered which allows more accurately predicting the next range bin (or sector) where the target can be after PRI seconds (i.e. at the next time instance). Thus, starting from the first element DPM(m,i=0) where the target has been located, if the speed is positive, the algorithm will check in the Draft Path Matrix if the element DPM(m−1,i+1), corresponding to the next time PRI and at the lower adjacent range bin, is higher than the element DPM(m,i+1) corresponding to the next time PRI but at the same range bin. If this is true, this implies that the target moved to the element DPM(m−1,i+1), otherwise it remained in the same range bin DPM(m−1,i+1). The comparison operation may be performed for each target over the whole Draft Path Matrix. If the speed was negative, the algorithm may check DPM(m,i+1) and DPM(m+1,i+1).

In one embodiment, the speed sign may be checked only at the beginning (namely i=0). In other embodiments, it is possible to check the speed sign for each element. Moreover, in the above-described embodiment, only two elements are checked for each time instance. However, in other embodiments, multiple elements (e.g., DPM(m−2,i+2), DPM(m−1, i+2), DPM(m,i+2), . . . ) may be considered for a more reliable tracking.

Based on the tracking algorithm, a Tracking Matrix may be formed. The Tracking Matrix may be a binary matrix, which may comprise ones ("1") for each element where a target has been at a specific time instance. The Tracking Matrix will only include determined positions of targets and any residues from static reflectors will be removed.

Figure 12:
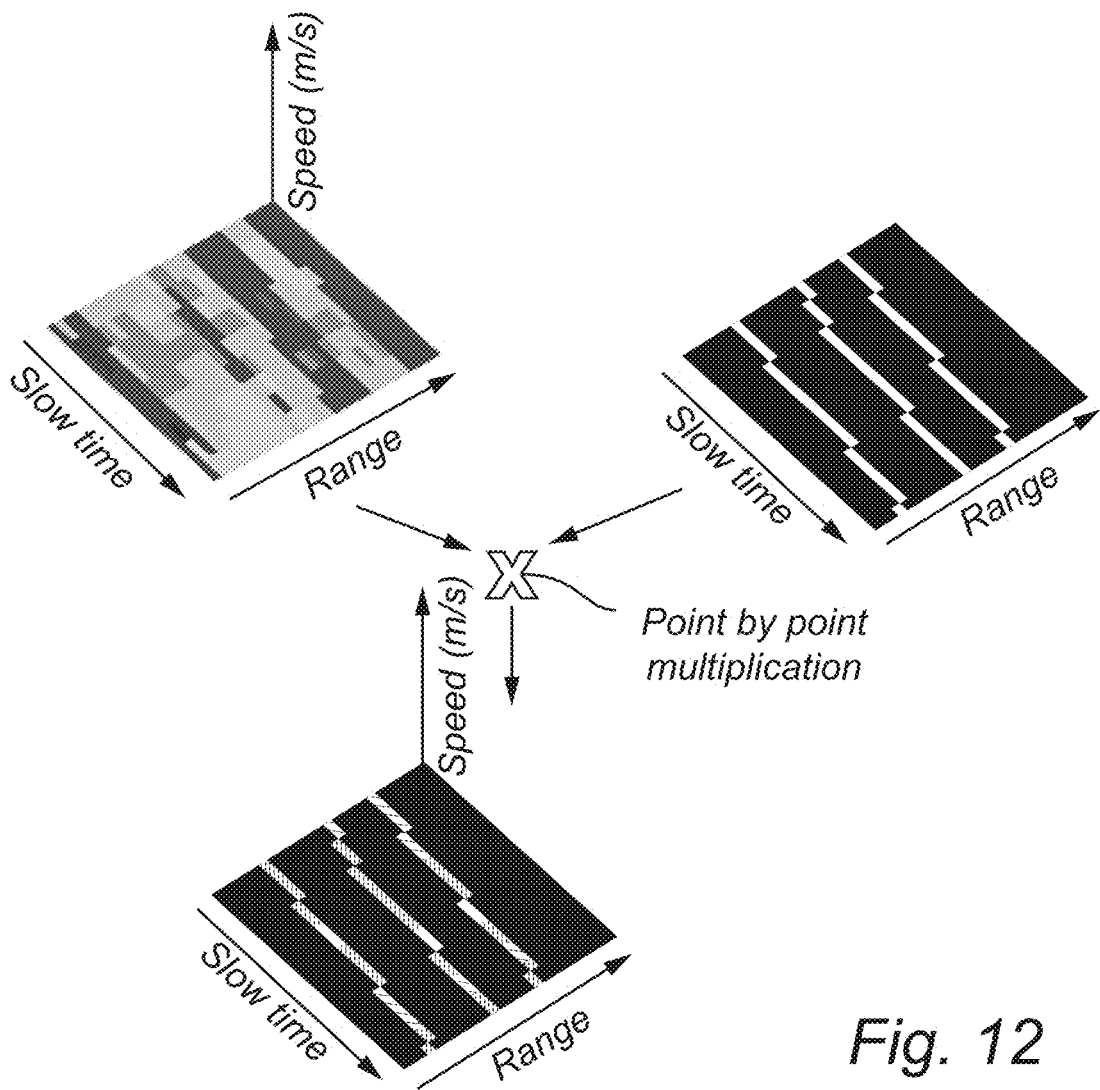
FIG. 12 is a scheme illustrating forming of a representation of tracks and speeds of targets.

As illustrated in FIG. 12, the resulted Tracking Matrix may thus be multiplied point by point by the Speed Matrix. Thus, a final speed profile may be obtained, which comprises information of speeds of movements of targets while being stripped of any residues due to static reflectors.

The process of determining speeds and positions of targets may be repeated periodically, based on a certain amount of data being acquired. For example, the process may be determined every 0.5-2 seconds. The repetition may be called a refresh operation, as the environment may be newly analyzed in each refresh operation. Thus, it is possible to update the number of targets and their speed information in a fair way over time.

If a target suddenly stops moving, it will be still present in the Tracking Matrix while it will disappear from the speed profile. After the refresh, the target will not be present anymore (neither in the Tracking Matrix nor in the Speed Matrix) because the DPM is generated considering also the speed information. However, it is also possible to exploit the matrices obtained before the current refresh to keep tracking/monitoring the target. This can be done because it is assumed that the target cannot instantaneously disappear from the monitored environment, so a target that is not moving in the previous Tracking Matrix may be assumed to be positioned in the sector in which the movement stopped also when the Tracking Matrix is refreshed.

However, there may be situations where the target leaves the environment (for example, if the target leaves a monitored room through a door). In this case, the target may be still considered to be present in the last tracked position with zero velocity. However, knowing that the target is not moving from the position for a while, it is possible to check vital signs information of the target. Based on the monitoring of the vital signs information, it may be determined whether a target is actually present in the tracked position. Also, a knowledge of doors/entrances/exits of the environment may be known such that, if a movement of a target stops in a position associated with a door/entrance/exit and no vital signs are detected, it may be considered highly likely that the target has left the environment.

As further explained below, even if the target does not move, it can still be detected by monitoring the vital signs.

It should be specified that at power-on of a system, if the target is stationary, the target will not be detected until it starts moving. When it starts moving, it will be detected by a new refresh operation. However, vital signs information may also be used for detecting stationary targets at power-on.

Figure 13A:
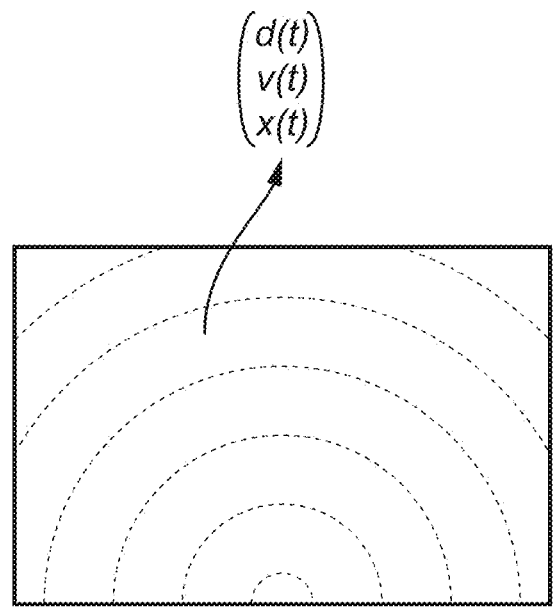
FIG. 13a is a schematic view of a division of an environment into sectors according to a first embodiment.
Figure 13B:
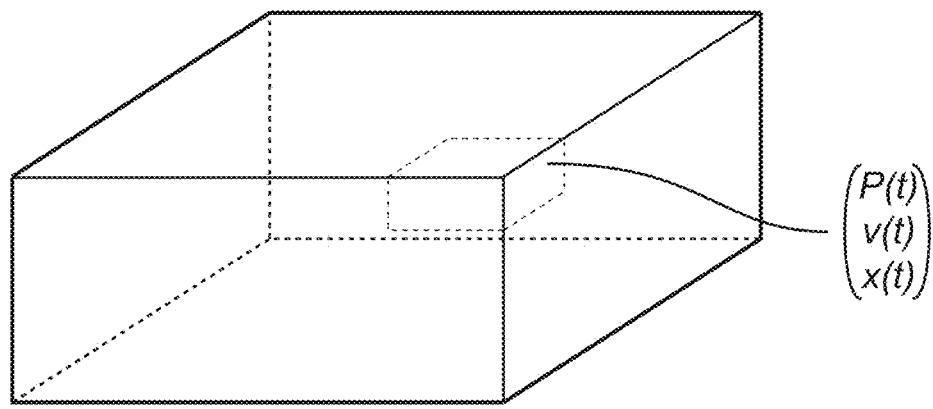
FIG. 13b is a schematic view of a division of an environment into sectors according to a second embodiment.

As explained above, multi-target tracking and monitoring may be performed under realistic conditions. As illustrated in FIGS. 13a-b, the tracking allows dividing an environment, e.g. a room, in sectors or cubes depending on the resolutions. In the first case, as illustrated in FIG. 13a, only a simple single sensor is used. Thus, distances to the transmitter may be determined, but it may not be possible to differentiate between targets at different angles to the sensor. In a second case, as illustrated in FIG. 13b, more advanced use of one or more sensor may be utilized. Thus, approaches as multiple-input and multiple-output (MIMO), beamforming, and wireless radar sensor network (WRSN) may be used, such that an environment may be divided into a large number of different sectors differentiating between targets in three dimensions. Depending on the design, the environment can be divided in different ways.

As mentioned above, the Doppler information from each sector (range bin) can be extracted, determining the phase of equation (7) over time. In this way, the Doppler shifts caused by the mechanical movements of heart and chest (lungs) x(t) can be detected and then heartbeat and respiration rate can be measured. This implies that when a target's position is determined, as explained above, it is possible to extract the mechanical movements x(t) from the Doppler information as:

$$\phi(t) = \frac{4\pi f_0}{c} x(t) \tag{18}$$

by which the vital signs can be monitored. The mechanical movements x(t) can be expressed as:

$$x(t) = x_r(t) + x_h(t) = X_r \sin(2\pi f_r t) + X_h \sin(2\pi f_h t) \tag{19}$$

where $x_r(t)$ and $x_h(t)$ indicate respectively the mechanical displacements produced by the respiration $x_r(t)$ and the heart $x_h(t)$ and are approximated as periodic functions, $X_r$ and $X_h$ are the maximum mechanical displacements of the lungs and the heart which are on average about 0.8 mm and 0.08 mm, respectively, while $f_r$ and $f_h$ are the vital signs frequencies which represent the information to be extracted. Depending on the subject and on the health condition, these frequencies are within 0.1-3 Hz.

For vital signs monitoring, it may normally be assumed that the targets are fixed at nominal distances in a quasistationary condition. This implies that normally they occupy one or few range bins (depending on the range resolution) and they experience the mechanical movements caused by the vital signs x(t). After the targets' positions are determined, the vital signs can be detected using equation (18) extracting the phase in the range bins where the targets are predicted.

The target position may be calculated based on determining movements of the target through the environment as explained above. An alternative way, which can be used for motionless targets (for which, of course, vital signs are still present) and which may be advantageously used as complementary to the determining of movements of the target through the environment, comprises checking a standard deviation of the phase for each range bin for a certain time. Vital signs involve a higher standard deviation than a stationary object and, hence, a target which does not move in the environment may in this way be detected and differentiated from stationary objects. The time interval for monitoring vital signs could be in the order of some seconds (e.g., >5 seconds) and therefore is longer than $T_d$ that may normally be used for tracking targets.

For each sector in the environment, the following information over time may be obtained if a target is present: d(t): absolute distance, p(t): position in three dimensions of the target, v(t): speed of target, x(t): vital signs. It is possible also to trigger an alarm if there is a fall incident and it is possible also to determine the location where the target has fallen.

The tracking of movements through the environment may thus be used for detection of falls. A fall may be detected based on definitions of changes in speeds of a target which are typical for a fall, such that speed changes may be compared to such definitions for determining whether a fall has occurred. Also, machine learning methods may be used for relating speed changes to falls and differentiating falls from normal movements.

During a fall, in fact, the speed continuously increases until the sudden moment when the fall stops abruptly. During a normal movement, the Doppler signal experiences a controlled movement. More precisely, while a person is sitting or lying down, the speed first gradually increases, and then decreases to a smooth stop, whereas during a walk, instead, the speed is quite constant over time. Thus, falls may be detected by determination of an increase in speed followed by an abrupt stop.

Furthermore, the determination of positions of targets may be used in order to improve detection of falls. Especially, in case of "soft" falls, where a person may collide with an object and/or slip slowly to the ground, the position of the target may be useful in reliably determining a fall. Thus, sectors close to the ground may be defined in the environment, such that if a target moves towards the ground and becomes fully positioned at sector(s) closest to the ground, the location of the target in such sector may be used for determining that a fall has occurred.

The position of the target may be used in combination with speed history in order to determine whether a fall has occurred.

Based on the above discussed monitoring and localization of targets, occurrence of specific events may be identified. Such events could be detection of falls, as explained above, detection of abnormalities in vital signs, detection of an intruder in the environment, etc. The monitoring of the environment may be set up to function autonomously, comparing detections of targets in the environment to pre-defined events. Thus, when occurrence of a pre-defined event is identified, an alert may be transmitted to an external unit or a notification may be output to a display. Thus, an operator may be notified when events occur, allowing the operator to further evaluate a situation and possibly take action. By sending out alerts when events occur, an operator may be responsible for monitoring developments in a large plurality of environments (such as several rooms) and the operator may be able to address focus to the monitored environment in which an alert has been triggered.

Figure 14:
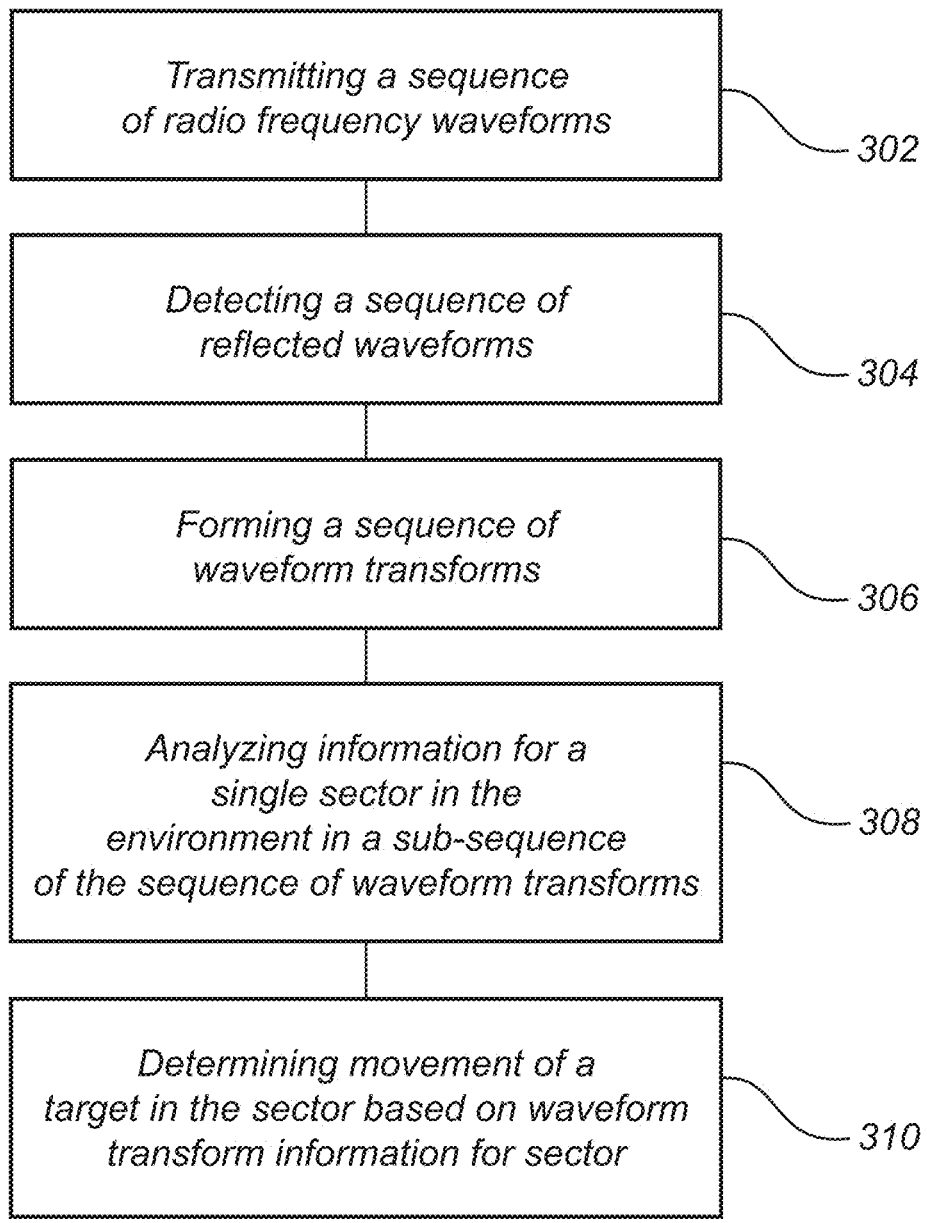
FIG. 14 is a flow chart of a method according to an embodiment.

Referring now to FIG. 14, a method for localization and monitoring of living being targets in an environment will be briefly summarized.

The method comprises transmitting 302 a sequence of radio frequency waveforms in the environment from a transmitter, wherein each of said radio frequency waveforms being a continuous-wave waveform modulated in frequency and/or phase. The transmitted waveforms may be reflected by targets (and stationary objects) in the environment.

The method further comprises detecting 304 a sequence of reflected waveforms, wherein each reflected waveform comprises a contribution of the transmitted waveform being reflected by a target and Doppler-shifted due to a movement of the target.

The method further comprises forming 306 a sequence of waveform transforms. Each waveform transform may be based on a single waveform in the sequence of reflected waveforms as mixed with the transmitted waveform to form a baseband signal. The waveform transform may comprise discretized information in a plurality of range bins, and wherein the information in a single range bin corresponds to reflections occurring at a specific sector in the environment in relation to the transmitter. Thus, reflections may be associated with a specific sector in the environment, enabling positions of targets to be determined.

The method further comprises analyzing 308 information for a single specific sector in a sub-sequence of the sequence of waveform transforms. Thus, by considering a sub-sequence of the waveform transforms, movements in a specific sector during a time interval may be determined.

The method further comprises determining 310 movement of a target in the specific sector based on the waveform transform information for that specific sector during a time period corresponding to the sub-sequence. The determined movement may be assigned to the entire sub-sequence as a dominant movement during the sub-sequence. The determined speeds and magnitudes of reflections from each sector may therefore be used for reliably ascertaining whether a target is positioned in a specific sector at a time instance, and differentiating targets from stationary objects in a real-life environment.

Figure 15:
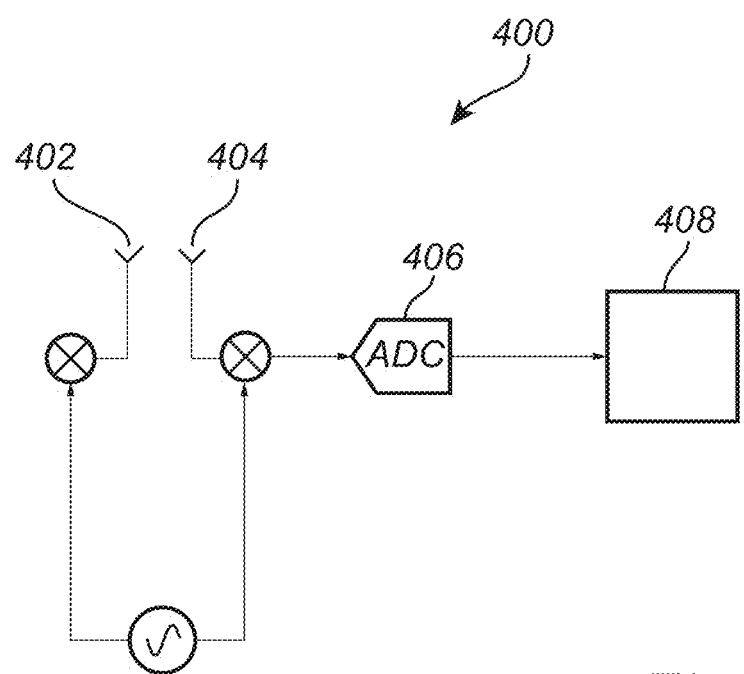
FIG. 15 is a schematic view of a system according to an embodiment.

Referring now to FIG. 15, a system 400 for localization and monitoring of living being targets in an environment will be described.

The system 400 comprises a transmitter 402 for transmitting a sequence of radio frequency waveforms in the environment from a transmitter 402, each of said radio frequency waveforms being a continuous-wave waveform modulated in frequency and/or phase.

The system 400 further comprises a receiver 404 for detecting a sequence of reflected waveforms, wherein each reflected waveform comprises a contribution of the transmitted waveform being reflected by a target and Doppler-shifted due to a movement of the target. The detected sequence of reflected waveforms may be mixed with a copy of the transmitted waveform to generate a baseband signal. The baseband signal may be digitized in an analog-to-digital converter 406. After digitization of the baseband signal, the baseband signal may be transferred to a processing unit 408, which may be configured to process the baseband signal.

The processing unit 408 may be configured to form a sequence of waveform transforms. The processing unit 408 may be configured to perform FFT on the digitized baseband signal (if an FMCW or SFCW waveform is used). Thus, information in a plurality of range bins may be formed corresponding to reflections occurring at a specific sector in the environment in relation to the transmitter. The processing unit 408 may further be configured to analyze information for a single specific sector in a sub-sequence of the sequence of waveform transforms, and determine movement of a target in the specific sector based on the waveform transform information for that specific sector during a time period corresponding to the sub-sequence.

The processing unit 408 may be arranged remotely from the transmitter 402 and the receiver 404 and may be arranged to receive information of the digitized baseband signal through wired or wireless communication. Alternatively, the processing unit 408 may be integrated in a common housing with the transmitter 402 and/or the receiver 404. Furthermore, the processing unit 408 may be distributed on a plurality of physical units performing different parts of the operations of the processing unit 408.

The processing unit 408 may be a central processing unit (CPU). The processing unit 408 may alternatively be a special-purpose circuitry for providing only specific logical operations. Thus, the processing unit 408 may be provided in the form of an application-specific integrated circuit (ASIC), an application-specific instruction-set processor (ASIP) or a field-programmable gate array (FPGA).

In an embodiment, there is provided a computer program product that provides instructions such that, when the computer program product is executed by the processing unit 408, the processing unit 408 may be caused to perform the desired processing of the received information.

In the above the inventive concept has mainly been described with reference to a limited number of examples. However, as is readily appreciated by a person skilled in the art, other examples than the ones disclosed above are equally possible within the scope of the inventive concept, as defined by the appended claims.

For instance, a variation of the frequency of a FMCW waveform is described so as to form a sawtooth wave based on FMCW waveforms. It should be realized that other variations of the modulation of the continuous wave may be realized. For instance, the transmitter frequency may be varied using a sinusoidal wave modulation, a triangle wave modulation, a square wave modulation (frequency shift keying), or a modulation increasing the transmitter frequency in discrete steps.

The invention claimed is:

1. A method for localization and monitoring of living being targets in an environment, the method comprising:
    transmitting a sequence of radio frequency waveforms in the environment from a transmitter, each of said radio frequency waveforms being a continuous-wave waveform modulated in frequency and/or phase;
    detecting a sequence of reflected waveforms, wherein each reflected waveform comprises a contribution of the transmitted waveform being reflected by a target and Doppler-shifted due to a movement of the target;
    forming a sequence of waveform transforms,
        wherein each waveform transform is based on a single waveform in the sequence of reflected waveforms,
        wherein the waveform transform comprises discretized information in a plurality of range bins,
        wherein the waveform transforms are Fourier transforms,
        wherein a single range bin of the plurality of range bins corresponds to a single frequency range in the Fourier transform, and
        wherein the information in a single range bin corresponds to reflections occurring at a specific sector in the environment in relation to the transmitter;
    analyzing information for a single specific sector in a sub-sequence of the sequence of waveform transforms; and
    determining movement of a target in the specific sector based on the waveform transform information for that specific sector during a time period corresponding to the sub-sequence; and
    combining the sequence of Fourier transforms with speed information in the specific sector in the environment to obtain a combined measure of speed and magnitude of reflection from targets in the specific sector,
    wherein the combined measure of speed and magnitude comprises a multiplication of the speed with the magnitude.

2. The method according to claim 1, wherein said analyzing comprises determining a peak frequency of a phase change in the sub-sequence for the specific sector, wherein the peak frequency is indicative of a speed of a target in the specific sector during the time period.

3. The method according to claim 1, further comprising comparing combined measures of speed and magnitude of reflection to at least one threshold for identifying targets in the environment.

4. The method according to claim 3, wherein a draft path of a target in the environment during a time period corresponding to the sequence of radio frequency waveforms is based on the combined measures of speed and magnitude of reflection, the method further comprising tracking a path of a target by analyzing selected potential positions of the target based on the combined measure at a time instance corresponding to a single waveform in relation to a determined position of the target at a previous time instance corresponding to a previous single waveform in the sequence of reflected waveforms.

5. The method according to claim 4, wherein the tracked path of a target is combined with speed information in the specific sector in the environment to obtain a speed profile of the target during a time period corresponding to the sequence of radio frequency waveforms.

6. The method according to claim 1, further comprising forming a number of groups of sub-sequences in the sequence of Fourier transforms, and performing said analyzing of information and determining of movement of a target for each group in said number of groups of sub-sequences.

7. The method according to claim 6, wherein length of a sub-sequence is selected based on a desired resolution of speed of targets.

8. The method according to claim 1, wherein analysis is based on a pre-defined number of detected reflected waveforms in the sequence, the method further comprising refreshing analysis of movements of target based on each sequence of a pre-defined number of detected reflected waveforms.

9. The method according to claim 8, wherein the sequence of reflected waveforms is used for vital signs monitoring based on a target that remains in a specific sector during at least a sub-sequence of the sequence of reflected waveforms.

10. The method according to claim 1, further comprising analyzing determined movement of a target for detecting falling of the target.

11. A system for localization and monitoring of living being targets in an environment, the system comprising:
   a transmitter for transmitting a sequence of radio frequency waveforms in the environment, each of said radio frequency waveforms being a continuous-wave waveform modulated in frequency and/or phase;
   a receiver for detecting a sequence of reflected waveforms, wherein each reflected waveform comprises a contribution of the transmitted waveform being reflected by a target and Doppler-shifted due to a movement of the target, and
   a processor for processing the detected sequence of reflected waveforms, said processor being configured to:
      form a sequence of waveform transforms,
         wherein each waveform transform is based on a single waveform in the sequence of reflected waveforms,
         wherein the waveform transform comprises discretized information in a plurality of range bins,
         wherein the waveform transforms are Fourier transforms,
         wherein a range bin corresponds to a single frequency range in the Fourier transform, and
         wherein the information in a single range bin corresponds to reflections occurring at a specific sector in the environment in relation to the transmitter;
      analyze information for a single specific sector in a sub-sequence of the sequence of waveform transforms; and
      determine movement of a target in the specific sector based on the waveform transform information for that specific sector during a time period corresponding to the sub-sequence; and
      combining the sequence of Fourier transforms with speed information in the specific sector in the environment to obtain a combined measure of speed and magnitude of reflection from targets in the specific sector, wherein the combined measure of speed and magnitude comprises a multiplication of the speed with the magnitude.

12. A computing device for localization and monitoring of living being targets in an environment, the computing device comprising:
   a processor for receiving and processing a detected sequence of reflected waveforms, said processor being configured to:
   form a sequence of waveform transforms,
   wherein each waveform transform is based on a single waveform in the sequence of reflected waveforms,
   wherein the waveform transform comprises discretized information in a plurality of range bins,
   wherein the waveform transforms are Fourier transforms,
   wherein a range bin corresponds to a single frequency range in the Fourier transform, and wherein the information in a single range bin corresponds to reflections occurring at a specific sector in an environment in relation to a transmitter;
   analyze information for a single specific sector in a sub-sequence of the sequence of waveform transforms, and
   determine movement of a target in the specific sector based on the waveform transform information for that specific sector during a time period corresponding to the sub-sequence; and
   combining the sequence of Fourier transforms with speed information in the specific sector in the environment to obtain a combined measure of speed and magnitude of reflection from targets in the specific sector, wherein the combined measure of speed and magnitude comprises a multiplication of the speed with the magnitude.

13. A computer program product comprising a non-transitory computer-readable medium comprising computer-readable instructions, which when executed on a processor cause the processor to process a detected sequence of reflected waveforms, said processing comprising:
   forming a sequence of waveform transforms,
      wherein each waveform transform is based on a single waveform in the sequence of reflected waveforms,
      wherein the waveform transform comprises discretized information in a plurality of range bins,
      wherein the waveform transforms are Fourier transforms,
      wherein a range bin corresponds to a single frequency range in the Fourier transform, and wherein the information in a single range bin corresponds to reflections occurring at a specific sector in an environment in relation to a transmitter;
   analyzing information for a single specific sector in a sub-sequence of the sequence of waveform transforms;
   determining movement of a target in the specific sector based on the waveform transform information for that specific sector during a time period corresponding to the sub-sequence; and
   combining the sequence of Fourier transforms with speed information in the specific sector in the environment to obtain a combined measure of speed and magnitude of reflection from targets in the specific sector,
   wherein the combined measure of speed and magnitude comprises a multiplication of the speed with the magnitude.

14. The method of claim 1, wherein the multiplication comprises a point by point matrix multiplication of elements of a speed matrix with magnitudes of elements of a range profile matrix.

15. The system of claim 11, wherein the multiplication comprises a point by point matrix multiplication of elements of a speed matrix with magnitudes of elements of a range profile matrix.

16. The computing device of claim 12, wherein the multiplication comprises a point by point matrix multiplication of elements of a speed matrix with magnitudes of elements of a range profile matrix.

* * * * *